United States Patent
Van Den Heuvel et al.

(10) Patent No.: US 10,037,412 B2
(45) Date of Patent: Jul. 31, 2018

(54) PATIENT HEALTH STATE COMPOUND SCORE DISTRIBUTION AND/OR REPRESENTATIVE COMPOUND SCORE BASED THEREON

(71) Applicant: KONINKLIJKE PHILIPS N.V., Eindhoven (NL)

(72) Inventors: Teun Van Den Heuvel, Waalre (NL); Lin Yang, Mesa, AZ (US); Nicolaas Lambert, Waalre (NL)

(73) Assignee: KONINKLIJKE PHILIPS N.V., Einhoven (NL)

( * ) Notice: Subject to any disclaimer, the term of this patent is extended or adjusted under 35 U.S.C. 154(b) by 184 days.

(21) Appl. No.: 15/025,758

(22) PCT Filed: Sep. 15, 2014

(86) PCT No.: PCT/IB2014/064509
§ 371 (c)(1),
(2) Date: Mar. 29, 2016

(87) PCT Pub. No.: WO2015/044826
PCT Pub. Date: Apr. 2, 2015

(65) Prior Publication Data
US 2016/0232323 A1    Aug. 11, 2016

Related U.S. Application Data

(60) Provisional application No. 61/884,347, filed on Sep. 30, 2013.

(51) Int. Cl.
*G06F 19/00* (2018.01)
*G06F 19/26* (2011.01)
*G16H 50/30* (2018.01)

(52) U.S. Cl.
CPC ......... *G06F 19/3431* (2013.01); *G16H 50/30* (2018.01)

(58) Field of Classification Search
None
See application file for complete search history.

(56) References Cited

U.S. PATENT DOCUMENTS 8,456,309 B2 *   6/2013   Sachanandani ...... A61B 5/0031
                                                    340/573.1
8,768,718 B2 *   7/2014   Cazares ................. G06Q 50/22
                                                      600/300
(Continued)

FOREIGN PATENT DOCUMENTS

| | | |
|---|---|---|
| JP | 2002095650 | 4/2002 |
| WO | 2012099534 A2 | 7/2012 |
| WO | 2013027027 | 2/2013 |

OTHER PUBLICATIONS

Tarassenko, et al., "Centile-based early warning scores derived from statistical distributions of vital signs", Resuscitation, Elsevier, IE, vol. 82, No. 8, Mar. 11, 2011; pp. 1013-1018.
(Continued)

*Primary Examiner* — Brian T Gedeon

(57) ABSTRACT

A method includes generating at least first and second histograms respectively for at least first and second sets of vital sign measurements using at least first and second predetermined bins. The first and second sets of the vital sign measurements each include at least two measurements acquired at different times, and the first and second vital sign are different vital signs. The method further includes generating a first score distribution for the first vital sign by mapping each bin of the first predetermined bins to a corresponding predetermined score. The method further includes generating a second score distribution for the second vital sign by mapping each bin of the second
(Continued)

predetermined bins to a corresponding predetermined score. The method further includes generating a compound score distribution for the first and second vital signs based on the first and second score distributions, the compound score distribution indicates a patient's health state.

20 Claims, 7 Drawing Sheets

(56) References Cited

U.S. PATENT DOCUMENTS

| | | | |
|---|---|---|---|
| 8,781,566 B2 * | 7/2014 | John | A61B 5/0452 600/509 |
| 2009/0093686 A1 | 4/2009 | Xiao | |
| 2012/0296675 A1 * | 11/2012 | Silverman | G06F 19/3431 705/3 |

OTHER PUBLICATIONS

Fullerton, et al., "Is the Modified Early Warning Score (MEWS) superior to clinical judgment in detecting critical illness in the pre-hospital environment?", Resuscitation, Elsevier, IE, vol. 83, No. 5, Jan. 9, 2012, pp. 557-562.

* cited by examiner

| Score | 3 | 2 | 1 | 0 | 1 | 2 | 3 |
|---|---|---|---|---|---|---|---|
| Respiratory rate | | ≤ 8 | | 9-14 | 15-20 | 21-29 | > 29 |
| Heart rate | | ≤ 40 | 41-50 | 51-100 | 101-110 | 111-129 | ≥ 129 |
| Systolic BP | ≤ 70 | 71-80 | 81-100 | 101-199 | | ≥ 200 | |
| Temperature | | ≤ 35 | 35.1-36 | 36.1-38 | 38.1-8.5 | ≥ 38.5 | |
| Neurological | | | | Alert | Voice | Pain | Unresp. |

FIG. 1

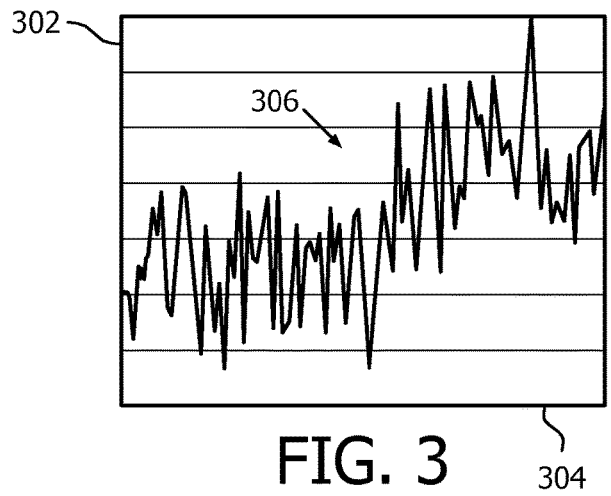
FIG. 3
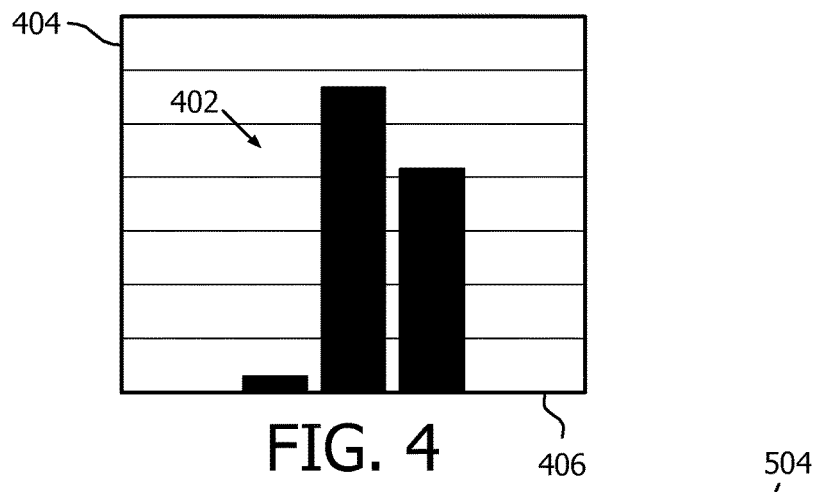
FIG. 4
| Score | 3 | 2 | 1 | 0 | 1 | 2 | 3 |
|---|---|---|---|---|---|---|---|
| Respiratory rate | | | | 5% | 61% | 35% | |
| Heart rate | | | 6% | 19% | 59% | 16% | |
| Systolic BP | | 41% | 48% | 11% | | | |
| Temperature | | | | 50% | 50% | | |
| Neurological | | | | 10% | 20% | 70% | |
FIG. 5

PATIENT HEALTH STATE COMPOUND SCORE DISTRIBUTION AND/OR REPRESENTATIVE COMPOUND SCORE BASED THEREON

CROSS-REFERENCE TO PRIOR APPLICATIONS

This application is the U.S. National Phase application under 35 U.S.C. § 371 of International Application No. PCT/IB2014/064509, filed on Sep. 15, 2014, which claims the benefit of U.S. Provisional Application Ser. No. 61/884,347, filed on Sep. 30, 2013. These applications are hereby incorporated by reference herein, for all purposes.

The following generally relates to monitoring a health state of a patient and more particularly to determining a patient health state of the patient through a patient health state compound score distribution and/or a representative compound score based thereon.

Patient heath state scores such as Early Warning and/or other scores are used in patient monitoring to help caregivers assess the severity of a patient's condition and their risk for deterioration. Such scores are typically based on singular observations of a set of vital signs. For example, in a hospital, a nurse may go room to room a couple times per shift (e.g., at the beginning and middle of their shift) and take vital signs such a respiratory rate, hear rate, systolic blood pressure, temperature, etc., and assess each patient's neurological condition through observation and questions.

The information from a round has been used to create an early warning score. An example of a prior art early warning score is shown in FIG. 1. This early warning score is in table or matrix form, with each column representing a specific score value, which is indicated in a header cell, each row representing a health state parameter (e.g., a vital sign), which is indicated in a header cell, and the cells in the body including criteria which maps a score value to a health state parameter. In this particular example, a patient with a respiratory rate of 17, a heart rate of 60, a systolic blood pressure of 90, and a temperature of 37, and who exhibits signs of "pain" has a score of 4 (or 1+0+1+0+2).

Unfortunately, this approach provides a narrow time snapshot (a single moment in time) of the patient's health state. Furthermore, this approach does not leverage all available information such as health state information obtained with a greater frequency, for example, through bed-side electronic device or monitors that continuously or periodically automatically measures health state parameters. In addition, going room to room and patient to patient and manually acquiring or invoking automatic acquisition of health state parameters consumes the health care givers' time, which could otherwise be used to provide patient care.

Aspects described herein address the above-referenced problems and others.

The following describes an approach in which sets of multiple different health state parameter measurements are used to determine a patient health state compound score distribution and/or a representative singular compound score based thereon. The compound score distribution and/or the representative singular compound score, in one instance, facilitates evaluation of a patient's health state.

In one aspect, a method includes generating at least first and second histograms respectively for at least first and second sets of vital sign measurements using at least first and second predetermined bins. The first and second sets of the vital sign measurements each include at least two measurements acquired at different times, and the first and second vital sign are different vital signs. The method further includes generating a first score distribution for the first vital sign by mapping each bin of the first predetermined bins to a corresponding predetermined score. The method further includes generating a second score distribution for the second vital sign by mapping each bin of the second predetermined bins to a corresponding predetermined score. The method further includes generating a compound score distribution for the first and second vital signs based on the first and second score distributions, the compound score distribution indicates a patient's health state.

In another aspect, a patient health state determiner includes at least one histogram generator that generates at least first and second histograms respectively for at least first and second sets of vital sign measurements using at least first and second predetermined bins. The first and second sets of the vital sign measurements each include at least two measurements acquired at different times, and the first and second vital sign are different vital signs. The patient health state determiner further includes an individual score distribution determiner that determines a first score distribution for the first vital sign by mapping each bin of the first predetermined bins to a corresponding predetermined score and a second score distribution for the second vital sign by mapping each bin of the second predetermined bins to a corresponding predetermined score. The patient health state determiner further includes a compound score distribution determiner that determines a compound score distribution for the first and second vital signs based on the first and second score distributions, wherein the compound score distribution indicates a health state of a patient.

In another aspect, a computer readable storage medium is encoded with computer readable instructions, which, when executed by a processor, cause the processor to: generate at least first and second histograms respectively for at least first and second sets of vital sign measurements using at least first and second predetermined bins. The first and second sets of the vital sign measurements each include at least two measurements acquired at different times. The first and second vital sign are different vital signs. The computer readable instructions, when executed by the processor, further cause the processor to generate a first score distribution for the first vital sign by mapping each bin of the first predetermined bins to a corresponding predetermined score. The computer readable instructions, when executed by the processor, further cause the processor to generate a second score distribution for the second vital sign by mapping each bin of the second predetermined bins to a corresponding predetermined score. The computer readable instructions, when executed by the processor, further cause the processor to generate a compound score distribution for the first and second vital signs based on the first and second score distributions. The compound score distribution indicates a health state of a patient.

The invention may take form in various components and arrangements of components, and in various steps and arrangements of steps. The drawings are only for purposes of illustrating the preferred embodiments and are not to be construed as limiting the invention.

FIG. 1 illustrates a prior art early warning score.

FIG. 2 schematically illustrates an example patient health state determiner, which includes a compound score distribution determiner, in connection with a subject and one or more health state parameter sensors.

FIG. 3 illustrates an example of a set of physiological measurements for a health state parameter acquired during a particular predefined time window.

FIG. 4 illustrates an example histogram generated for the set of measurements of FIG. 3.

FIG. 5 illustrates example individual score distribution based on the histograms for multiple different health state parameters.

Figure 6:
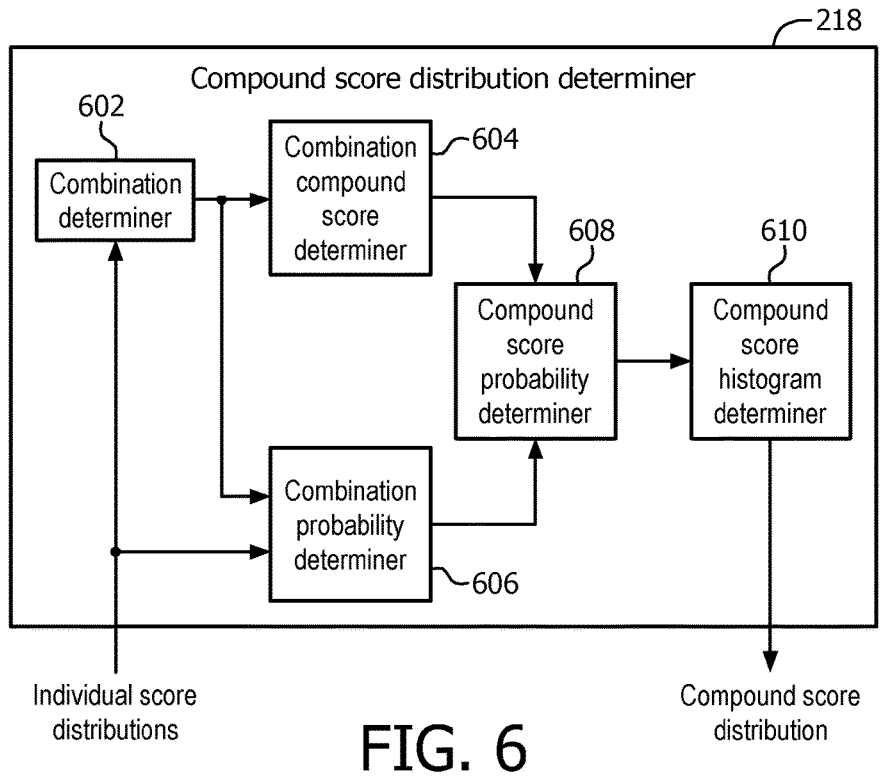

FIG. 6 schematically illustrates an example of the compound score distribution determiner.

Figure 7:
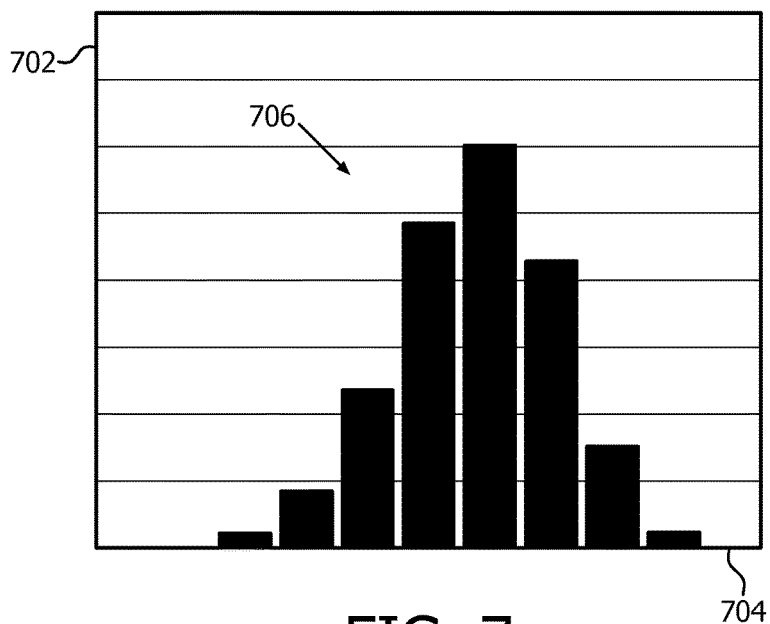

FIG. 7 schematically illustrates an example of a compound score distribution.

Figure 2:
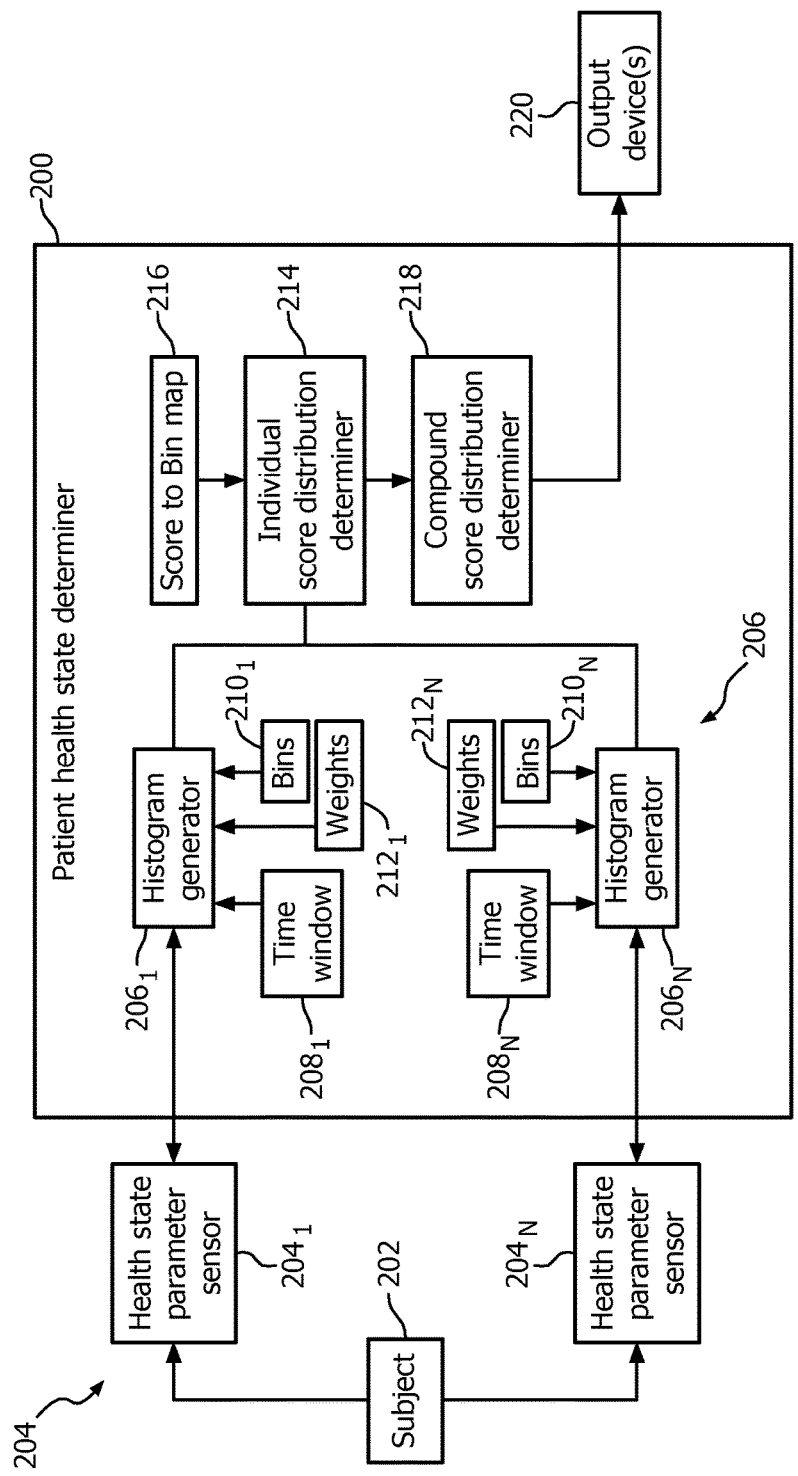
Figure 8:
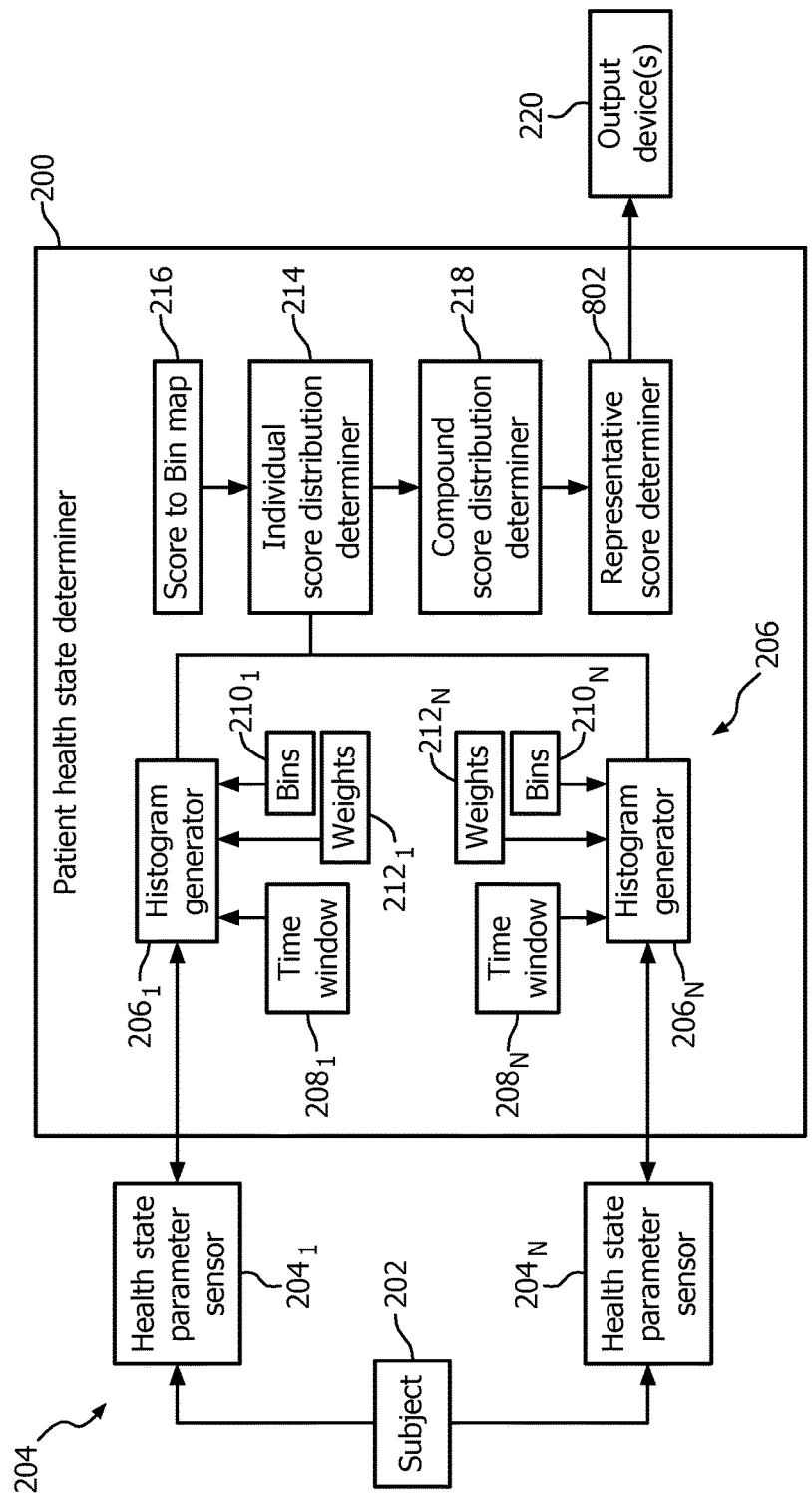

FIG. 8 schematically illustrates a variation of FIG. 2 including a representative compound score determiner.

Figure 9:
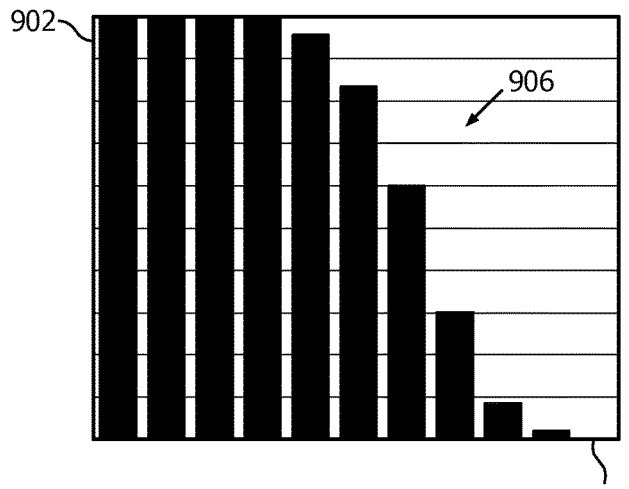

FIG. 9 illustrates an example cumulative compound score histogram.

Figure 10:
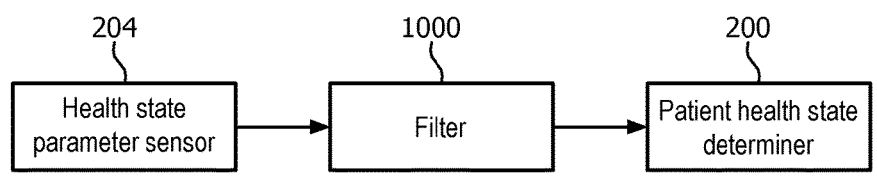

FIG. 10 schematically illustrates a variation of FIG. 2 or 3, including a filter.

Figure 11:
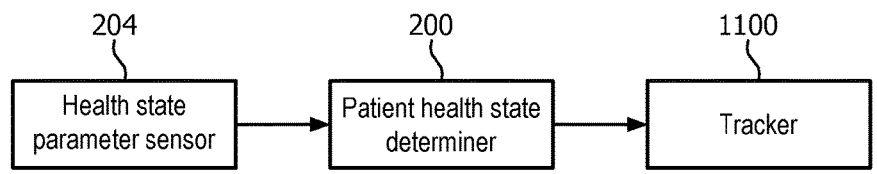

FIG. 11 schematically illustrates a variation of FIG. 2, 3 or 10, including a tracker.

Figure 12:
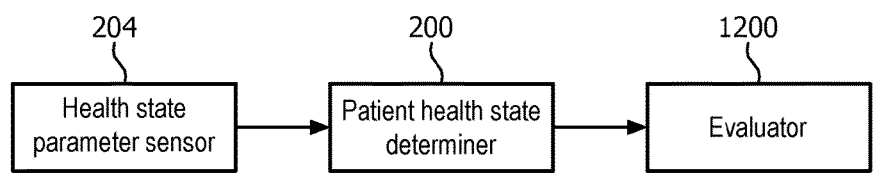

FIG. 12 schematically illustrates a variation of FIG. 2, 3, 10 or 11, including an evaluator.

Figure 13:
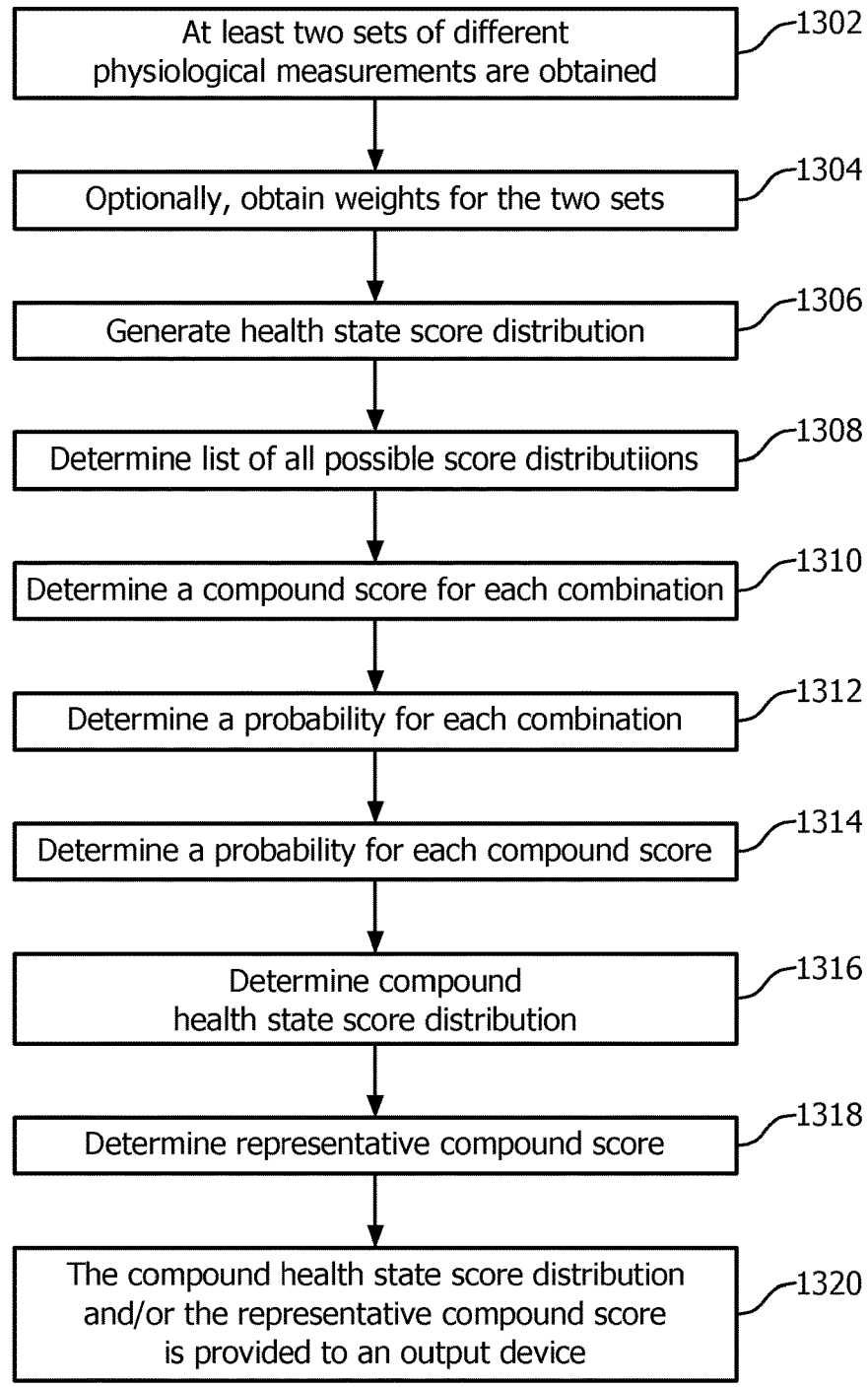

FIG. 13 illustrates another example method in accordance with the examples herein.

The following describes an approach for determining a health state metric a compound score distribution from sets of scorable measured patient health state parameters. Optionally, a representative singular compound score based thereon. The health state metric can additionally or alternatively be used otherwise to assess an uncertainty of a patient's status, development of patient's status over time, among other characteristics. Algorithms for deriving singular per-observation scores from singular observations, for deriving a singular compound score from singular observations/singular per-observation scores, and/or other algorithms can be used with this approach.

FIG. 2 schematically illustrates an example patient health state determiner 200 in connection with a subject 202 (e.g., human or animal) and N health state parameter sensors 204, including a health state parameter sensor $204_1$, . . . , a health state parameter sensor $204_N$ (where N is an integer equal to or greater than one).

At least one of the health state parameter sensors 204, in one instance, senses health state information such as, but not limited to, one or more of a systolic blood pressure, a respiratory rate, a heart rate, or a temperature. For example, a health state parameter sensor of the health state parameter sensors 204 may include a (non-invasive or invasive) blood pressure monitor, etc. The frequency at which a health state parameter sensor 204 senses depends on the particular health state parameter being sensed.

Optionally, a health state parameter sensor of the health state parameter sensors 204 includes a camera (still and/or video), an audio recorder, etc. which senses subject movement, behavior, emotion, etc., and/or speech, sound, etc. Such information can be evaluated by a computer and/or a human to determine a neurological state of the subject such as whether they are alert, unresponsive, talking, in pain, etc. A human can also make observations and enter the observations into a health state parameter sensor 204.

The health state parameter sensors 204 generate electrical signals indicative of the sensed health state parameters. The signals can be analog and/or digital signals. Analog signal can be converted to digital signals. Where the signals are conveyed to a device external to the health state parameter sensors 204, such conversion can be performed by the health state parameter sensors 204 and/or a device (e.g., an analog to digital converter) external to the health state parameter sensors 204.

The analog and/or digital signals can be stored in computer memory of the N health state parameter sensors 204 (as shown), in computer memory of a central monitory station, in computer memory of a data repository (e.g., in an electronic medical record of the subject, etc.), in computer memory of the patient health state determiner 200, and/or in other computer memory. Such memory may store all signals, only signals during a particular (e.g., most recent) predetermined time window, etc.

The health state parameter sensors 204 may be part of a same device such as a multi-parameter monitor. Alternatively, at least two of the health state parameter sensors 204 are part of a same device and at least one of the health state parameter sensors 204 is part of a different device. Alternatively, each of the at least two of the health state parameter sensors 204 are part of a different device. Examples of such devices include, but are not limited to a blood pressure monitor, a heart rate monitor, a thermometer, a respiratory rate monitor, oxygen saturation monitor etc.

The patient health state determiner 200 includes a plurality of histogram generators 206, including a histogram generator $206_1$, . . . , a histogram generator $206_N$. In a variation, the histogram generators 206 are implemented through a single histogram generator 206. In a variation, the histogram generators 206 are implemented through a multivariate histogram generator, which generates a probability function for multiple sensors. In the illustrated example, each of the health state parameter sensors 204 is associated with a corresponding one of the histogram generators 206 such that the health state parameter sensor $204_1$ is in communication with the histogram generator $206_1$, . . . , the health state parameter sensor $204_N$ is in communication with the histogram generator $206_N$.

Such communication includes conveying signals there between. By way of example, the histogram generator $206_1$ may send a request signal to the health state parameter sensor $204_1$ for a certain time block of stored sensed signals, and, in response, obtains the signals from the health state parameter sensor $204_N$. By way of another example, the histogram generator $206_1$ accesses the memory of the health state parameter sensor $204_1$ and obtains the certain time block of stored sensed signals. The time blocks may be the same or different for two different the histogram generator 206.

Each of the histogram generators 206 obtains sensed signals corresponding to a predetermined time window. For example, the histogram generator $206_1$ obtains sensed signals based on a time window $208_1$, . . . , the histogram generator $206_N$ obtains sensed signals based on a time window $208_N$. As discussed above, the health state parameter sensors 204 may sense (acquire, sample, etc.) at different frequencies. As such, a same or a different number of samples may be obtained from each of the health state parameter sensors 204.

Briefly turning to FIG. 3, an example set of samples for a time window is illustrated. In FIG. 3, a y-axis 302 represents respiratory rate, an x-axis 304 represents time, and a curve 306 represents respiratory rate as a function of time. The curve 306 is generated by connecting the individual samples, using linear, spline, and/or other interpolation approaches. As an example, the samples can be for a time window ranging from one hour in the past up to the current time.

Returning to FIG. 2, the histogram generators 206 generate histograms with the obtained signals. Each of the histogram generators 206 employs a corresponding set of bins. The bins of a particular histogram may depend on the health state parameter being sensed and can be based on a default, user defined, etc. In the illustrated example, the histogram generator $206_1$ employs bins $210_1, \ldots,$ the histogram generator $206_N$ employs bins $210_N$.

In the illustrated embodiment, each of the histogram generators 206 employs a set of weights for generating a histogram. In the illustrated example, the histogram generator $206_1$ employs weights $212_1, \ldots,$ the histogram generator $206_N$ employs weights $212_N$. The weights for a particular histogram may depend on the health state parameter being sensed and can be based on a default, user defined, etc.

In one instance, the weights weight samples as a function of time, with a lowest weight value for the oldest acquired sample and a highest weight value for a most recent acquired sample. In this instance, the weight may vary there between linearly or non-linearly. Other weighting functions are also contemplated herein. In another instance, the weights can all be one (1) or omitted.

Briefly turning to FIG. 4, an example weighted histogram 402 based on the samples of FIG. 3 is illustrated. A y-axis 404 represents sample value and the x-axis 406 represents the bins. For this example, the oldest samples are weighted with a value of zero and the weighting linearly increases with time. The bins, in this example, are similar to those in FIG. 1 for respiratory rate. However, the bins can be different. The histogram 402 represents the distribution of the samples based on the bins.

Returning to FIG. 2, an individual score distribution determiner 214 determines a score distribution for each of the N histograms (i.e., the histograms from the N histogram generators 206) based on a pre-determined score to bin map 216, which provides a mapping between scores and each of the bins of the histograms, defining a score/bin pair for each health state parameter. Briefly turning to FIG. 5, an example table or matrix of individual score distributions for each of a plurality of example health state parameters is shown.

In FIG. 5, each row 502 represents a different health state parameter, and each column 504 represents a score for a health state parameter value. A first row in FIG. 5 represents respiratory rate. The illustrated distribution is from the histogram 402 of FIG. 4, with the bins assigned to the scores in a manner similar to that in FIG. 1. With the histogram 402, 5% of the samples are in the range 9-14, which corresponds to a score of 1, 61% of the samples are in the range 15-20, which corresponds to a score of 0, and 35% of the samples are in the range 21-29, which corresponds to a score of 1.

In FIG. 5, a score of zero represents a "normal" range. Scores increasing therefrom (e.g., 1, 2, and 3) represents respiratory rate values outside of the normal" range, either below (left side of zero) or above (right side of zero). Other scoring systems, other bins, other mappings between bins and scores, etc. can be utilized. FIG. 5 also shows score distributions for heart rate, systolic blood pressure, temperature, and neurological.

Returning to FIG. 2, a compound score distribution determiner 218 determines a compound score distribution based on the individual score distributions. Various approaches can be employed. For example, in one non-limiting instance, a compound score distribution is determined by calculating multiple scores, each corresponding to (e.g., central values derived from) a subset of health parameter observations, and subsequently calculating a distribution for the multiple scores.

Other approaches are also contemplated herein. For example, another non-limiting example is described in connection with FIG. 6. In this non-limiting example, a combination determiner 602 receives, as an input, the individual score distributions. The combination determiner 602 determines, from the individual score distributions, all possible score combinations. For example, with respect to FIG. 5, the combination determiner 602 determines all possible combinations for the fifteen entries in the table for the five health state parameters.

A combination compound score determiner 604 determines a compound score for each combination based on the different combinations from the combination determiner 602. For instance, continuing the example in the previous paragraph, there is one combination with an aggregate score of zero all zeros. For an aggregate score combination of one, there are six combinations. These combinations include a score of one for one of the health state parameters and a score of zero for all of the other health state parameters. The other combinations are not discussed in detail for sake of brevity but are readily apparent based on the discussion herein.

A combination probability determiner 606 determines a probability of each combination based on the different combinations from the combination determiner 602 and the input individual score distributions. For instance, continuing the example in the previous two paragraphs, there is one combination with an aggregate score of zero. For this combination, the score distribution is 5%, 19%, 11%, 50% and 10%. The combination probability determiner 606 determines a probability of this combination as the product of the score distribution, or (0.05)(0.19)(0.11)(0.50)(0.10).

A compound score probability determiner 608 determines a probability of each compound score based on the combination compound scores and the combination probabilities. For instance, continuing the example in the previous three paragraphs, there are six combinations with an aggregate score of one and hence six combination probabilities, one for each of the six combinations. For this, the compound score probability determiner 608 determines a probability as the sum of the individual probabilities of the six score combinations.

A compound score histogram determiner 610 determines a compound score distribution or histogram based on the probabilities for each compound score. Briefly turning to FIG. 7, an example compound score distribution 706 is illustrated. In this example, a y-axis 702 represents compound score probability, and an x-axis 704 represents compound scores. Returning to FIG. 2, the patient health state determiner 200 outputs the compound score distribution. In the illustrated example, the compound score distribution is a summation of the per health state parameter scores. In other instance, other approaches can be utilized.

In the illustrated embodiment, the compound score distribution is provided to one or more output devices 220. The one or more output devices 220 may include a display monitor, a data repository, a central monitoring station, a smartphone, a computer, a decision support system such as a clinical decision support system, and/or other device. In one non-limiting instance, a histogram similar to FIG. 7 is visually displayed via a display monitor. Optionally, a list of actions is visually presented along with the table. In this case, the visually displayed information indicates suggested action(s) for each compound score distribution.

Turning to FIG. 8, a variation of FIG. 2 is illustrated. In this variation, the patient health state determiner 200 further includes a representative score determiner 802. The representative score determiner 802 identifies a representative singular compound score to represent the patient. In this instance, the singular compound score is visually presented via one of the output devices 220 in addition or in alternative to the compound score distribution and/or list of suggest actions.

In one instance, the representative score can be based on a cumulative compound score distribution. A non-limiting example of a cumulative compound score distribution 906 is shown in FIG. 9. In FIG. 9, a y-axis 902 represents cumulative probably and an x-axis 904 represents compound scores. In FIG. 9, a summation of the distribution for that value and higher is provided for each score value. This distribution may be used to derive a representative score, e.g., in one instance, the representative score is the highest score value with a cumulative probability higher than 50%.

The compound score distribution can be used to establish a distribution (as opposed to a singular value) of a deterioration score to represent the status of a patient. Such a distribution can in turn be used to derive the single representative value, but may also be used in other ways such as to assess the uncertainty of a patient's status, development of patient's status over time, among other characteristics. The patient health state determiner 200 can be part of a medical device such as a patient monitoring device and/or a general purpose or dedicate computer.

FIG. 10 illustrates a variation which includes a filter 1000. The filter 1000, in one non-limiting instance, filters the signals from the health state parameter sensors 204 based on a predetermined time range or time threshold. For example, the filter 1000, in one instance, can be configured to filter out signals older than predetermined date D and/or predetermined time T. The particular date and/or time may or may not vary from health state parameter to health state parameter. The filter 1000, in this example, is external to the patient health state determiner 200. However, in another variation, at least a portion of the filter 1000 is part of the patient health state determiner 200.

FIG. 11 illustrates a variation which includes a tracker 1100. The tracker 1100, in one non-limiting instance, is configured to track score distribution and/or representative score for the current status of a patient over time. The tracker 1100, in this example, is external to the patient health state determiner 200. However, in another variation, at least a portion of the tracker 1100 is part of the patient health state determiner 200.

FIG. 12 illustrates a variation which includes an evaluator 1200. The evaluator 1200, in one non-limiting instance, evaluates historical and current score distribution and/or representative score for the current status of a patient. This may include comparing the score distribution between different time windows (e.g. the past hour vs. the same time frame yesterday; the past hour vs. the past 24 hours; the past hour vs. the hour before that, etc.). When the recent past is to be compared to the past, equal weights may be used for all observations within both time frames. The evaluator 1200, in this example, is external to the patient health state determiner 200.

However, in another variation, at least a portion of the evaluator 1200 is part of the patient health state determiner 200. In a variation, the comparison of the score distribution to a patient population can also be considered. For example, the sore distribution can be compared to a similar patient population stay in a same institute in a same season in a previous year. This allows for considering the seasonal patient population change.

Another variation includes a combination of FIGS. 10, 11 and/or 12, and/or other variation.

The method of the present invention can be made part of a patient monitoring system, or be implemented on a computer system that interfaces with a patient monitoring system, among other possibilities.

FIG. 13 illustrates an example method.

It is to be appreciated that the ordering of the acts is not limiting. As such, other orderings are contemplated herein. In addition, one or more acts may be omitted and/or one or more additional acts may be included.

At 1302, at least two sets of different physiological measurements are obtained, each set including at least two measurements acquired at at least two different times.

At 1304, optionally, at least two sets of weights, one set for each of the two sets of different physiological measurements, are obtained.

At 1306, a health state score distribution is generated for each of the at least two sets of different physiological measurements, optionally using the at least two sets of weights.

At 1308, a list of all possible score combinations is determined based on the individual health state score distributions.

At 1310, a compound score for each combination is determined based on the list of all possible score combinations.

At 1312, a probability for each combination is determined based on the individual health state score distributions and the list of all possible score combinations.

At 1314, a probability for each compound score is determined based on the compound score for each combination and the probability for each combination.

At 1316, compound health state score distribution is determined based at least on the probability for each combination.

At 1318, optionally, a representative compound score is determined based on the compound health state score distribution.

At 1320, the compound health state score distribution and/or optional representative compound score is provided to an output device.

The above acts may be implemented by way of computer readable instructions, encoded or embedded on computer readable storage medium (i.e., physical memory and other non-transitory medium), which, when executed by a microprocessor(s), cause the processor(s) to carry out the described acts. Additionally or alternatively, at least one of the computer readable instructions is carried by a signal, carrier wave and other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for determining a patient health state compound score distribution, comprising:
acquiring at least first and second sets of vital sign measurements of a patient;
generating at least first and second histograms respectively for the at least first and second sets of vital sign measurements using at least first and second predetermined bins,
wherein the first and second sets of the vital sign measurements each include at least two measurements acquired at different times, and the first and second vital sign are different vital signs;

generating a first score distribution for the first vital sign by mapping each bin of the first predetermined bins to a corresponding predetermined score;

generating a second score distribution for the second vital sign by mapping each bin of the second predetermined bins to a corresponding predetermined score;

generating a compound score distribution for the first and second vital signs based on the first and second score distributions, wherein the compound score distribution indicates a health state of the patient; and displaying the generated compound score distribution with a list of suggested actions for each possible score.

2. The method of claim 1, further comprising:
storing the generated compound score.

3. The method of claim 1, wherein generating the at least first and second histograms includes weighting vital sign measurements based on acquisition time.

4. The method of claim 1, wherein generating the compound score distribution includes:
identifying all possible score combinations based on the first and second score distributions;
determining a compound score for each combination based on the identified score combinations;
determining a probability for each combination based on the first and second score distributions and the identified score combinations;
determining a probability for each compound score based on the probability for each combination; and
determining the compound score distribution based on the probability for each compound score.

5. The method of claim 4, wherein determining the probability for a compound score includes summing the individual probabilities of the score combinations for the compound score.

6. The method of claim 1, further comprising:
determining a representative compound score based on the compound score distribution.

7. The method of claim 6, wherein the representative compound score, for each score value, is a summation of the distribution for that value and higher values.

8. The method of claim 6, wherein the representative compound score is a single value.

9. The method of claim 6, further comprising:
visually presenting the representative compound score.

10. The method of claim 1, further comprising:
filtering the at least first and second sets of vital sign measurements to remove measurements that were acquired before a predetermined time duration from a current time.

11. The method of claim 1, further comprising:
tracking the compound score distribution over time.

12. The method of claim 1, further comprising:
comparing at least two compound score distributions determined at at least two different times.

13. A patient health state determiner, comprising:
a computer;
a non-transitory computer readable storage medium storing computer readable instructions that when executed by the computer perform operations including:
generating at least first and second histograms respectively for at least first and second sets of vital sign measurements of a patient using at least first and second predetermined bins, wherein the first and second sets of the vital sign measurements each include at least two measurements acquired at different times, and the first and second vital sign are different vital signs;

determining a first score distribution for the first vital sign by mapping each bin of the first predetermined bins to a corresponding predetermined score and a second score distribution for the second vital sign by mapping each bin of the second predetermined bins to a corresponding predetermined score; and determining a compound score distribution for the first and second vital signs based on the first and second score distributions, wherein the compound score distribution indicates a health state of the patient; and a display configured to display the compound score distribution with a list of suggested actions for each possible score.

14. The patient health state determiner of claim 13, further comprising:
a storage configured to store the compound score distribution.

15. The patient health state determiner of claim 13, wherein the generating of the at least first and second histograms includes weighting vital sign measurements based on acquisition time.

16. The patient health state determiner of claim 13, wherein the determining of the compound score distribution includes:
identifying all possible score combinations based on the first and second score distributions;
determining a compound score for each combination based on the identified score combinations;
determining a probability for each combination based on the first and second score distributions and the identified score combinations;
determining a probability for each compound score based on the probability for each combination; and
determining the compound score distribution based on the probability for each compound score.

17. The patient health state determiner of claim 13, wherein the determining of the compound score distribution sums the first and second score distributions to compute the compound score distribution.

18. The patient health state determiner of claim 13, wherein said operations further include:
determining a single value representative compound score based on the compound score distribution.

19. The patient health state determiner of claim 13, wherein said operations further include at least one of:
filtering the at least first and second sets of vital sign measurements to remove measurements that were acquired before a predetermined time duration from a current time;
tracking the compound score distribution over time; and
comparing at least two compound score distributions determined at least at two different times.

20. A non-transitory computer readable storage medium encoded with computer readable instructions, which, when executed by a processor, causes the processor to:
generate at least first and second histograms respectively for at least first and second sets of vital sign measurements of a patient using at least first and second predetermined bins,
wherein the first and second sets of the vital sign measurements each include at least two measurements acquired at different times, and the first and second vital sign are different vital signs;
generate a first score distribution for the first vital sign by mapping each bin of the first predetermined bins to a corresponding predetermined score;

generate a second score distribution for the second vital sign by mapping each bin of the second predetermined bins to a corresponding predetermined score;

generate a compound score distribution for the first and second vital signs based on the first and second score distributions, wherein the compound score distribution indicates a health state of the patient; and control a display to display the compound score distribution with a list of suggested actions for each possible score.

* * * * *